(12) United States Patent
Lee et al.

(10) Patent No.: US 10,265,027 B2
(45) Date of Patent: Apr. 23, 2019

(54) BIOSIGNAL PROCESSING METHOD AND BIOSIGNAL PROCESSING APPARATUS

(71) Applicant: SAMSUNG ELECTRONICS CO., LTD., Suwon-si (KR)

(72) Inventors: Moonsook Lee, Seoul (KR); Jinyoung Park, Hwaseong-si (KR); Seongho Cho, Gwacheon-si (KR); Woochang Lee, Anyang-si (KR); Juneyoung Lee, Seongnam-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 127 days.

(21) Appl. No.: 14/665,482

(22) Filed: Mar. 23, 2015

(65) Prior Publication Data
US 2016/0058389 A1    Mar. 3, 2016

(30) Foreign Application Priority Data
Aug. 27, 2014   (KR) .................. 10-2014-0112332

(51) Int. Cl.
*A61B 5/00* (2006.01)
*A61B 5/0205* (2006.01)
*A61B 5/145* (2006.01)
*A61B 5/0402* (2006.01)
*A61B 5/11* (2006.01)
(Continued)

(52) U.S. Cl.
CPC ........ *A61B 5/7221* (2013.01); *A61B 5/02055* (2013.01); *A61B 5/681* (2013.01); *A61B 5/7246* (2013.01); *A61B 5/01* (2013.01); *A61B 5/021* (2013.01); *A61B 5/0402* (2013.01); *A61B 5/0488* (2013.01); *A61B 5/1102* (2013.01); *A61B 5/14532* (2013.01); *A61B 5/14546* (2013.01); *A61B 5/4872* (2013.01); *A61B 5/4875* (2013.01); *A61B 2560/0252* (2013.01); *A61B 2560/0257* (2013.01)

(58) Field of Classification Search
None
See application file for complete search history.

(56) References Cited

U.S. PATENT DOCUMENTS 6,016,435 A     1/2000   Maruo et al.
6,640,117 B2   10/2003   Makarewicz et al.
(Continued)

FOREIGN PATENT DOCUMENTS

KR   1020130010207 A    1/2013
KR   1020130107066 A   10/2013
KR      101357098 B1    2/2014

OTHER PUBLICATIONS

Yoshida S. et al., "Metabolism of fatty acids and lipid hydroperoxides in human body monitoring with Fourier transform Infrared Spectroscopy", Lipids in Health and Disease 2009, vol. 8, No. 28, 11 pages total, URL: http://www.lipidworld.com/content/8/1/28.
(Continued)

*Primary Examiner* — John R Downey
(74) *Attorney, Agent, or Firm* — Sughrue Mion, PLLC

(57) ABSTRACT

A biosignal processing apparatus and a biosignal processing method are provided. The biosignal processing method includes: detecting a biosignal of a subject; detecting status information; and determining a correlation between the biosignal and the status information.

18 Claims, 6 Drawing Sheets

(51) Int. Cl.
   *A61B 5/0488* (2006.01)
   *A61B 5/021* (2006.01)
   *A61B 5/01* (2006.01)

(56) References Cited

U.S. PATENT DOCUMENTS

| | | | | |
|---|---|---|---|---|
| 2002/0123671 | A1* | 9/2002 | Haaland | A61B 5/0002 600/300 |
| 2003/0013947 | A1 | 1/2003 | Frattarola | |
| 2004/0073093 | A1* | 4/2004 | Hatlestad | A61B 5/1116 600/300 |
| 2005/0088296 | A1* | 4/2005 | Lee | G08B 21/02 340/539.12 |
| 2005/0113703 | A1* | 5/2005 | Farringdon | A61B 5/0428 600/509 |
| 2008/0262374 | A1* | 10/2008 | Gerber | A61B 5/01 600/547 |
| 2009/0156924 | A1* | 6/2009 | Shariati | A61B 5/7475 600/365 |
| 2009/0270700 | A1 | 10/2009 | Van Herpen et al. | |
| 2010/0056873 | A1* | 3/2010 | Allen | A61B 5/002 600/300 |
| 2010/0152546 | A1* | 6/2010 | Behan | A61B 5/0002 600/301 |
| 2010/0152600 | A1* | 6/2010 | Droitcour | A61B 5/05 600/534 |
| 2010/0318424 | A1* | 12/2010 | LaValle | G06F 19/3418 705/14.58 |
| 2011/0213229 | A1* | 9/2011 | Benoit | G01N 33/725 600/345 |
| 2011/0230732 | A1* | 9/2011 | Edman | G09B 5/00 600/301 |
| 2012/0041279 | A1* | 2/2012 | Freeman | A61B 5/0205 600/301 |
| 2012/0095303 | A1 | 4/2012 | He | |
| 2013/0314243 | A1 | 11/2013 | Le | |
| 2014/0343380 | A1* | 11/2014 | Carter | A61B 5/7246 600/309 |
| 2014/0378794 | A1* | 12/2014 | Conrad | A61B 5/681 600/317 |
| 2015/0106020 | A1* | 4/2015 | Chung | G06F 19/3418 702/19 |

OTHER PUBLICATIONS

Berger et al., "Multicomponent blood analysis by near-infrared Raman spectroscopy", Applied Optics, vol. 38, No. 13, May 1, 1999, p. 2916-2926.

* cited by examiner

BIOSIGNAL PROCESSING METHOD AND BIOSIGNAL PROCESSING APPARATUS

RELATED APPLICATION

This application claims priority from Korean Patent Application No. 10-2014-0112332, filed on Aug. 27, 2014 in the Korean Intellectual Property Office, the disclosure of which is incorporated herein in its entirety by reference.

BACKGROUND

1. Field

Methods and apparatuses consistent with exemplary embodiments relate to biosignal processing for providing correlation information between a biosignal and status information that influences the biosignal.

2. Description of the Related Art

Recently, the interest in health has increased rapidly and rates of adult diseases have also increased. Thus, the demand for and supply of devices capable of individually monitoring a user's health is also increasing. Examples of such devices may include blood sugar sensors and blood pressure sensors. In the case of a patient who has diabetes or blood-pressure-related diseases, the condition of the patient needs to be frequently checked and continuously managed. Therefore, much research has been conducted to provide compact measurement devices capable of frequently checking physical conditions of patients, without the patients having to visit hospitals. In particular, much research has been conducted to provide mobile health-care systems using applications of mobile phones, for example, smartphones.

Environmental factors, such as temperature, may affect a health condition of a person that can be measured and monitored by biosignals of the person. If a biosignal of the person is provided along with information of a correlation between factors that influence the biosignal, the person may be able to monitor his or her own physical conditions more effectively.

SUMMARY

Exemplary embodiments provide biosignal processing methods and biosignal processing apparatuses for providing a correlation between a biosignal and status information that influences the biosignal.

According to an aspect of an exemplary embodiment, there is provided a biosignal processing method including: detecting a biosignal of a subject; detecting status information; and determining a correlation between the biosignal and the status information.

The determining may include determining the correlation in response to the status information being determined as having a probability of influencing the biosignal of the subject.

The determining may further include determining that the status information has the probability of influencing the biosignal on a lookup table indicating that the status information corresponds to the detected biosignal.

The biosignal of the subject may be detected in a non-invasive manner.

The biosignal may include at least one of information about an amount of a material contained in the subject and information about a motion of an object contained in the subject.

The biosignal may include information about at least one of blood sugar, cholesterol, body fat, blood pressure, an electrocardiogram, ballistocardiography, photoplethysmography, and an electromyogram of the subject.

The status information may vary according to an external environment.

The status information may include at least one of a temperature of an external environment, a humidity of the external environment, an atmospheric pressure of the external environment, a body water of the subject, a body temperature of the subject, and a motion of the subject.

The correlation may represent a degree of a change in the biosignal according to a change in the status information.

The correlation may represent a range of the status information corresponding to a reference range of the biosignal.

The determining of the correlation may include: generating a biosignal pattern based on using the biosignal in time domain; generating a status information pattern based on the status information in the time domain; and determining a correlation value between the biosignal pattern and the status information pattern.

The biosignal processing method may further include correcting the biosignal pattern based on the status information pattern.

The biosignal processing method may further include displaying at least one of the status information, the biosignal, and the correlation.

According to an aspect of another exemplary embodiment, there is provided a biosignal processing apparatus including: a first sensor configured to detect a biosignal of a subject; a second sensor configured to detect status information; and a processor configured to determine a correlation between the biosignal and the status information.

The processor is further configured to determine the correlation in response to the status information being determined as having a probability of influencing the biosignal.

The biosignal processing apparatus may further include a controller configured to control the first sensor based on the status information and the correlation.

When the status information is in a reference range, the controller may activate the first sensor to detect the biosignal.

The reference range may correspond to an abnormal range of the biosignal.

The first sensor may detect the biosignal of the subject in a non-invasive manner.

The biosignal may include at least one of information about an amount of a material contained in the subject and status information of an object contained in the subject.

The biosignal may include information about at least one of blood sugar, cholesterol, and body fat, blood pressure, an electrocardiogram, ballistocardiography, photoplethysmography, and an electromyogram of the subject.

The status information may vary according to an external environment.

The biosignal processing apparatus may further include a display configured to display at least one of the status information, the biosignal, and the correlation.

The biosignal processing apparatus may further include a memory configured to store a lookup table indicating that the status information corresponds to the detected biosignal, wherein the processor is further configured to determine the correlation in response the biosignal being indicated as corresponding to the status information in the lookup table.

BRIEF DESCRIPTION OF THE DRAWINGS

The above and/or other aspects will become apparent and more readily appreciated from the following description of exemplary embodiments, taken in conjunction with the accompanying drawings in which.

DETAILED DESCRIPTION

Figure 1:
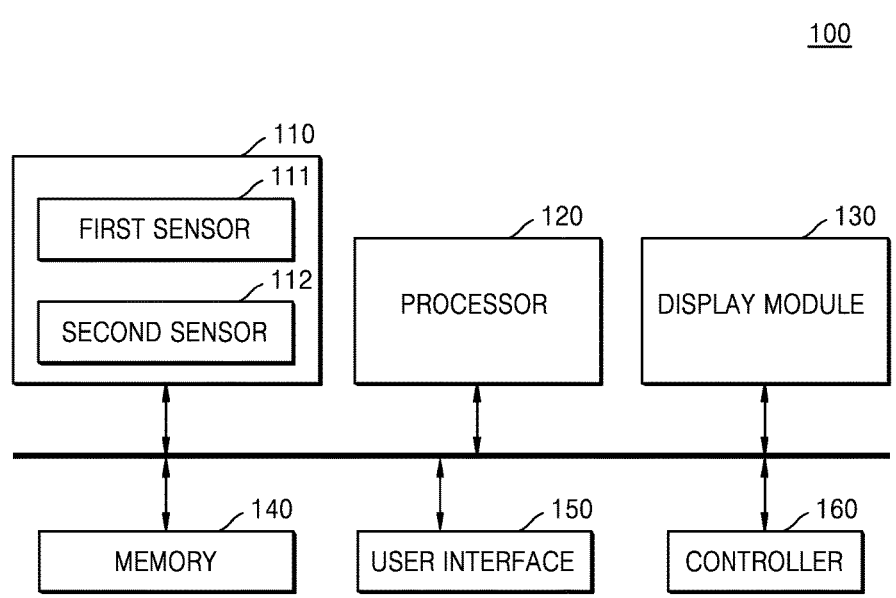
FIG. 1 is a block diagram of a biosignal processing apparatus according to an exemplary embodiment.

Reference will now be made in detail to exemplary embodiments, examples of which are illustrated in the accompanying drawings, wherein like reference numerals refer to like elements throughout. In this regard, the present exemplary embodiments may have different forms and should not be construed as being limited to the descriptions set forth herein. Accordingly, the exemplary embodiments are merely described below, by referring to the figures, to explain aspects. As used herein, the term "and/or" includes any and all combinations of one or more of the associated listed items.

FIG. 1 is a block diagram of a biosignal processing apparatus 100 according to an exemplary embodiment. As shown in FIG. 1, the biosignal processing apparatus 100 may include a sensor 110 that detects a biosignal and status information of a user of the biosignal processing apparatus 100, a processor 120 that determines a correlation between the biosignal and the status information by using the biosignal and the status information received from the sensor 110, a display module (i.e., display) 130 that displays at least one selected from the group consisting of the biosignal, the status information, and the correlation, a user interface 150 that receives a user input or the like, a memory 140 that stores a program to be used in the biosignal processing apparatus 100, and a controller 160 that controls internal components of the biosignal processing apparatus 100.

The biosignal processing apparatus 100 may be implemented using a single housing. The biosignal processing apparatus 100 may be a device capable of being carried by the user. For example, the biosignal processing apparatus 100 may be a wearable device. In addition, the biosignal processing apparatus 100 may be implemented using a plurality of housings. In a case where the biosignal processing apparatus 100 is implemented using a plurality of housings, components may be connected to one another by wire or wireless. The biosignal processing apparatus 100 may be implemented using a partial configuration of a device that performs a different function, for example, a mobile terminal.

The sensor 110 may include a first sensor 111 that detects the biosignal, and a second sensor 112 that detects the status information. For example, the sensor 110 may be worn on a user's wrist, chest, or ankle.

A biosignal is a signal in a subject such as, for example, a human, an animal, or a body part of the human or the animal, which can be continually measured and monitored. The biosignal is a unique signal generated from the subject. For example, the biosignal may be a signal based on a movement of a specific part (for example, a heart or a muscle) of the subject, such as an electrocardiogram (ECG), a ballistocardiogram (BCG), a photoplethysmograph (PPG), an electromyogram, or a blood pressure, and the biosignal may be information about an amount of materials included in the subject, for example, blood sugar, cholesterol, and body fat. The user may be the subject from which a biosignal is to be measured, but the user is a medical expert having an ability to use the biosignal processing apparatus 100. That is, the user may be a broader concept than the subject.

The first sensor 111 may detect the biosignal in a non-invasive manner. The first sensor 111 may include a plurality of electrodes. The plurality of electrodes may contact the subject when the subject wears the first sensor 111. The first sensor 111 may detect the biosignal by measuring an electrical property based on a change in the biosignal. For example, the first sensor 111 may detect the biosignal by measuring a change in a resistance. Besides the electrodes, the first sensor 111 may detect the biosignal by using a light beam, such as an infrared ray.

The second sensor 112 may detect the status information. The status information is a factor that influences the biosignal and may act as a noise upon acquisition of the biosignal. The status information may be different from the biosignal detected by the first sensor 111. Alternatively, the status information may be information about an external environment, such as a temperature, a humidity, and an atmospheric pressure, or information about a subject's motion, body temperature, and body water. When the second sensor 112 detects a biosignal different from the biosignal detected by the first sensor 111, the second sensor 112 may detect the biosignal in a non-invasive manner and may be a sensor including an electrode, a light beam, or the like. When the status information is the information about the external environment, the second sensor 112 may include a humidity sensor, a temperature sensor, and a pressure sensor. In addition, when the status information is the information about the subject's motion, the second sensor 112 may be an acceleration sensor, a gyro sensor, and a terrestrial magnetic sensor. When the status information is the information about the subject's body temperature, the second sensor 112 may be a temperature sensor. When the status information is the information about the subject's body water, the second sensor 112 may be an optical sensor.

The processor 120 may calculate a correlation between the biosignal and the status information, which will be described below.

The display module 130 may display information processed by the biosignal processing apparatus 100. For example, the display module 130 may display a user interface (UI) or a graphical user interface (GUI) so as to display at least one selected from the group consisting of the biosignal, the status information, and the correlation. The display module 130 may include at least one selected from the group consisting of a liquid crystal display (LCD), a thin film transistor-liquid crystal display (TFT-LCD), an organic light-emitting diode (OLED), a flexible display, and a three-dimensional (3D) display. Two or more display modules 130 may be provided, depending on an implementation mode of the biosignal processing apparatus 100.

The display module may constitute a touch screen by forming a mutual layer structure together with a touch pad that receives a user input. In a case where the display module 130 and the touch pad form the mutual layer structure to thereby constitute the touch screen, the display module 130 may also be used as an input device as well as an output unit. In an exemplary embodiment, the display module 130 constituted as the touch screen may automatically start to measure the biosignal when a user touch input is detected in a certain region.

The memory 140 may store data generated during operations of the biosignal processing apparatus 100. According to an exemplary embodiment, the memory 140 is a general storage medium and may include a hard disk drive (HDD), a read only memory (ROM), a random access memory (RAM), a flash memory, and a memory card. In a case where the status information acts as a noise of the biosignal, a correction algorithm for correcting the biosignal by using the status information may be prestored in the memory 140. In addition, the correlation calculated by the processor 120 may be stored in the memory 140. The memory 140 may store a lookup table that matches various status information to each type of biosignals that may be affected by the status information. For example, the lookup table may indicate that status information representing outside temperature matches to a biosignal representing a blood sugar level measured from a user of the biosignal processing apparatus 100. In this case, the lookup table may allow the processor 120 to determine the outside temperature as a factor that the processor 120 is to use in calculating a correlation when the user's blood sugar level is measured.

The user interface 150 may receive an input for operating the biosignal processing apparatus 100 from the user, and may output at least one selected from the group consisting of the biosignal, the status information, and the correlation processed by the biosignal processing apparatus 100. The user interface 150 may include a button, a keypad, a switch, a dial, or a touch interface, which allows the user to directly operate the biosignal processing apparatus 100. The user interface 150 may include a display unit that displays an image and may be implemented using a touch screen. According to another exemplary embodiment, the user interface 150 may include an I/O port that connects human interface devices (HIDs). The user interface 150 may include an I/O port that inputs or outputs an image.

The controller 160 may control an overall operation of the biosignal processing apparatus 100. For example, the controller 160 may control the sensor 110 to measure the biosignal. In addition, the controller 160 may analyze the detected biosignal, determine whether the detected biosignal is normal, and provide the result to the user through the display module 130. When analyzing the biosignal, the controller 160 may correct the detected biosignal by using the status information. In addition, the memory 140 may store status information corresponding to a biosignal that is determined as being present in an abnormal range by using the correlation.

On the other hand, the processor 120 may use the biosignal and the status information to calculate a correlation between the biosignal and the status information. The biosignal may be distorted by various factors. For example, an electrocardiogram (ECG) and a blood sugar may be distorted by the subject's motion or an external temperature. In addition, the degree of the distortion of the ECG and the blood sugar may be different for each subject. For example, while a blood sugar of a certain subject is sensitive to the subject's motion, a blood sugar of a certain subject may not be sensitive to a subject's motion. In this manner, if providing an individual with the status information sensitive to the biosignal, the individual may simply predict the change in the biosignal from the change in the status information.

Figure 2:
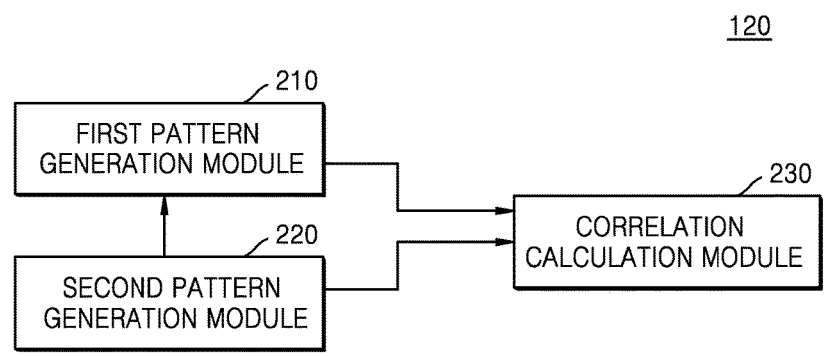
FIG. 2 is a block diagram of a processor of FIG. 1 according to an exemplary embodiment.

FIG. 2 is a block diagram of the processor 120 of FIG. 1 according to an exemplary embodiment. As shown in FIG. 2, the processor 120 may include a first pattern generation module 210 that generates biosignal pattern, a second pattern generation module 220 that generates status information pattern, and a correlation calculation module 230 that generates a correlation between the biosignal and the status information.

The first pattern generation module 210 may generate the biosignal pattern by using the biosignal. The biosignal pattern may be a function representing a continuous change in the biosignal over time. For example, in a case where the biosignal is an ECG signal, the first pattern generation module 210 may amplify an ECG signal received from the first sensor 111 and filter the amplified ECG signal by using a finite-impulse response (FIR) bandpass filter. Then, the first pattern generation module 210 may generate an ECG signal pattern by detecting peaks from the filtered ECG signal and adaptively filtering the detected peaks. In addition, in a case where the biosignal is blood sugar information, the second pattern generation module 220 may receive blood sugar information from the first sensor 111, filter the received blood sugar information, and generate a blood sugar pattern representing a continuous change in the blood sugar over time.

The second pattern generation module 220 may generate the status information pattern by using the status information. The status information pattern may be a function representing a change in the status information over time. For example, when the status information is the subject's motion, the second pattern generation module 220 may receive the motion information from the second sensor 112. The second pattern generation module 220 may calculate vector magnitudes of X, Y, and Z components from the motion information and filter the calculated vector magnitudes by using a bandpass filter. Then, the second pattern generation module 220 may generate a motion information pattern by detecting motion peaks from the filtered signal and adaptively filtering the detected peaks. The motion peak may be a signal generated when the motion occurs. In addition, in a case where the status information is temperature information, the second pattern generation module 220 may receive temperature information from the second sensor 112, filter the received temperature information, and generate a temperature information pattern representing a change in temperature over time.

On the other hand, when generating the biosignal pattern, the first pattern generation module 210 may correct the biosignal pattern by using the status information. For example, when the subject moves during the detection of the ECG signal, the motion information may be included in the signal detected through the first sensor 111. Therefore, the first pattern generation module 210 may generate an ECG signal pattern by removing a noise signal generated from the user's motion taken at the time the ECG signal was detected from the first sensor 111. In addition, a resistance of the subject may be different according to temperature. Therefore, even when the first sensor 111 detects a blood sugar, the detected result may be different according to a temperature of the subject. The first pattern generation module 210 may correct a blood sugar information pattern by using the temperature information.

The correlation calculation module 230 may calculate a correlation between the biosignal and the status information by using the biosignal pattern and the status information pattern. The correlation may be information representing the degree at which the status information influences the biosignal. The correlation calculation module 230 may calculate a correlation value between the biosignal pattern and the status information pattern. When the correlation value is equal to or greater than a predetermined value, the controller 160 may determine that the correlation between the biosignal pattern and the status information pattern is high and may output the result through the display module 130.

The correlation calculation module 230 may calculate the correlation between the biosignal pattern and the status information pattern during whole time, but may calculate the correlation between the biosignal pattern of a reference range, for example, an abnormal range, and the status information pattern corresponding thereto. For example, the correlation calculation module 230 may calculate, from a temperature pattern, a temperature distribution of a case where the blood pressure is in an abnormal range, and calculate a correlation value between the blood pressure of the abnormal range and the temperature distribution corresponding thereto. When the correlation value is equal to or greater than a predetermined value, the controller 160 may determine that the correlation between the blood pressure pattern and the temperature pattern is high and may output the result through the display module 130.

Figure 3:
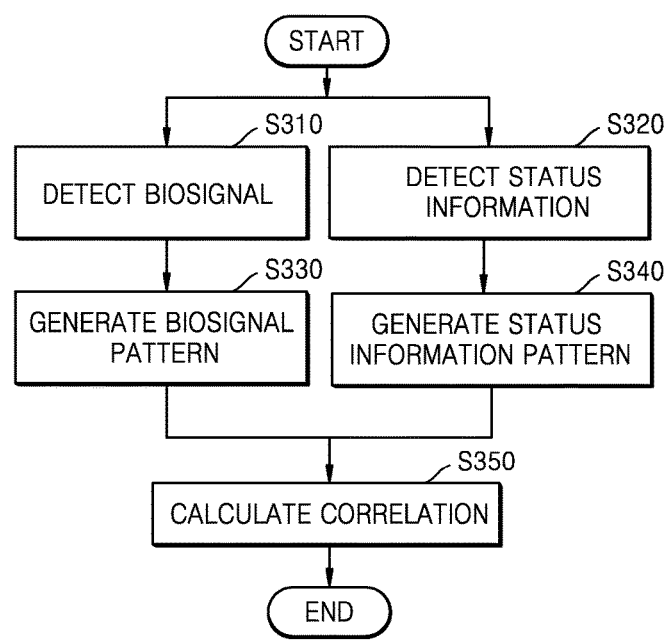
FIG. 3 is a flowchart of a method of calculating a correlation between status information and a biosignal, according to an exemplary embodiment.

FIG. 3 is a flowchart of a method of calculating a correlation between status information and a biosignal, according to an exemplary embodiment. As shown in FIG. 3, the first sensor 111 may detect a biosignal (S310). The first sensor 111 may detect the biosignal of a subject in a non-invasive manner by using an electrode, a light beam, or the like. The biosignal may include information about an amount of a material contained in the subject and/or information about a motion of an object contained in the subject. For example, the biosignal may include information about an amount of at least one selected from blood sugar, cholesterol, and/or body fat, which is contained in the subject, and/or information about at least one selected from blood pressure, an ECG, ballistocardiography (BCG), photoplethysmography (PPG), and an electromyogram (EMG).

The second sensor 112 may detect status information (S320). The status information is a factor that influences the biosignal. The status information may be a biosignal different from the biosignal detected by the first sensor 111, information about an external environment, or information about a motion of the subject itself. For example, the status information may include at least one selected from the group consisting of a temperature of the external environment, a humidity of the external environment, an atmospheric pressure of the external environment, a body water of the subject, a body temperature of the subject, and a motion of the subject.

The first pattern generation module 210 of the processor 120 may generate a biosignal pattern based on time by using the biosignal received from the first sensor 111 (S330). In addition, the second pattern generation module 220 may generate a status information pattern based on time by using the status information received from the second sensor 112 (S340). When the above-described patterns are generated, the detected information may be filtered by using a low pass filter, an adaptive filter, or the like. The first pattern generation module 210 may correct the biosignal pattern by using the status information pattern.

The correlation calculation module 230 of the processor 120 may calculate a correlation between the biosignal pattern and the status information pattern (S350). The correlation may refer to a change in the biosignal according to a change in the status information. When there are various types of status information patterns detected by the second pattern generation module 210, the correlation calculation module 230 may determine one or more status information pattern which correspond to the biosignal pattern based on the lookup table stored in the memory 140. The correlation calculation module 230 may calculate the correlation by calculating a correlation value between the biosignal pattern and the status information pattern. For example, if the first pattern general module 120 detects a biosignal indicating the blood pressure of the user and the second pattern generation module 210 detects the current temperature, humidity, and pressure of the external environment, the calculation module 230 may determine that the current temperature is the only factor corresponding to the blood pressure based the lookup table, and calculate a correlation between the blood pressure and the current temperature without calculating a correlation between the blood pressure and the humidity or the pressure. When the correlation value is equal to or greater than a reference value, the controller may determine that the correlation between the biosignal and the status information is high. The correlation may include a range of the status information corresponding to the biosignal of an abnormal range.

Figure 4:
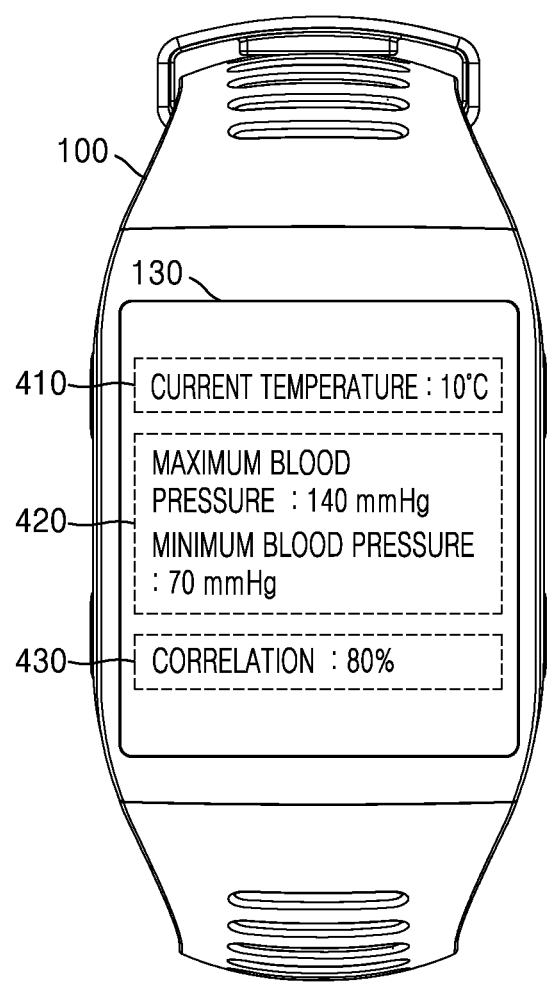
FIGS. 4 and 5 are reference diagrams for explaining a method of displaying a correlation between status information and a biosignal, according to an exemplary embodiment.
Figure 5:
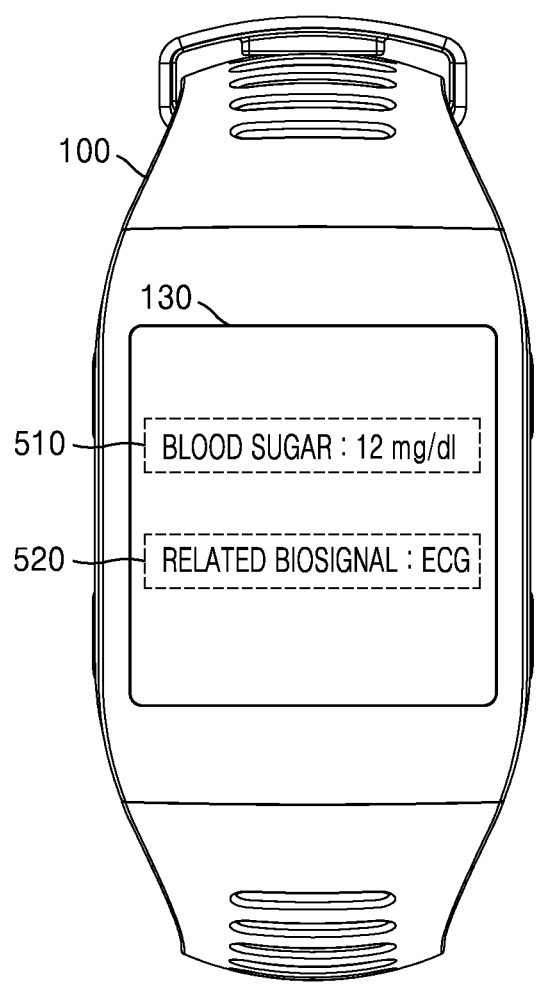

The calculated correlation or the like may be provided to the user through the display module 130 or the like. FIGS. 4 and 5 are reference diagrams of a method of displaying the correlation between the status information and the biosignal, according to an exemplary embodiment. As illustrated in FIG. 4, the display module 130 may display a temperature as the status information 410 and a maximum blood pressure and a minimum blood pressure as the biosignal 420, and may also display a correlation 430 numerically. In this way, the user may confirm the correlation between his or her blood pressure and the temperature. Hence, the user may recognize that he or she has to pay more attention to the blood pressure when a temperature is greatly changed.

If a plurality of sensors are all operated to detect the biosignal, an overload may occur in the signal processing. Therefore, the user may activate only one of the plurality of sensors. For example, the user may activate a sensor that detects a blood sugar. As illustrated in FIG. 5, the biosignal processing apparatus 100 may detect a blood sugar and display a detection result 510 on the display module 130. In addition, the biosignal processing apparatus 100 may provide a type of a biosignal 520 that is necessary to take care of according to a current blood sugar value, or a type of a biosignal that may be abnormal. As the type of the biosignal 520 that is necessary to take care of, an ECG is displayed in FIG. 5. This is because the correlation between the blood sugar and the ECG is stored in the biosignal processing apparatus 100 according to the exemplary embodiment. In the above case, in the exemplary embodiment, the blood sugar is the status information and the ECG is the biosignal. The user may recognize from the blood sugar value that a problem occurs in the ECG, and may activate an ECG detection sensor to measure the ECG. The activation of the biosignal detection sensor may be performed by a user command, but may be automatically performed by the biosignal processing apparatus 100 by using the above-described correlation.

Figure 6:
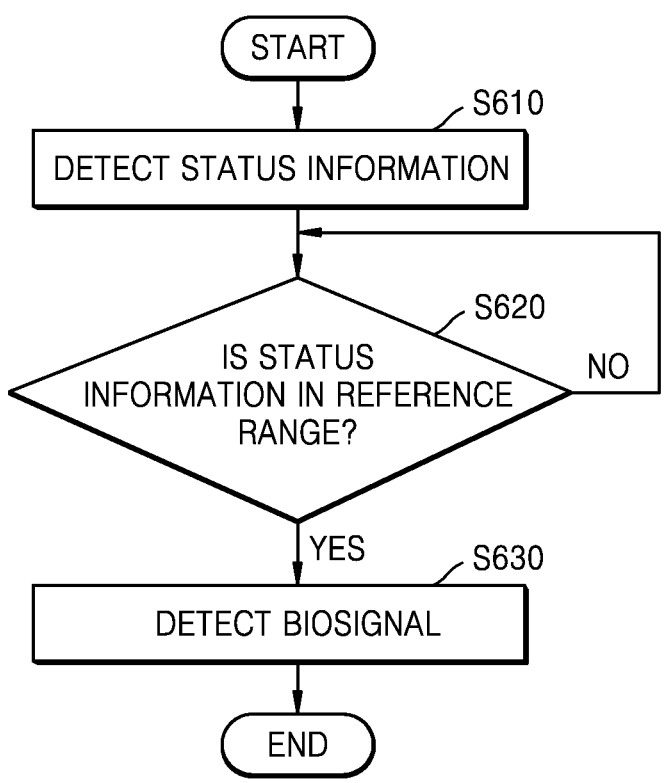
FIG. 6 is a flowchart of a method of measuring a biosignal based on status information, according to an exemplary embodiment.

FIG. 6 is a flowchart of a method of measuring a biosignal based on status information, according to an exemplary embodiment. As shown in FIG. 6, the second sensor 112 may detect status information (S610). The status information is a factor that influences the biosignal and may be information about an external environment or a different biosignal.

The controller 160 may determine whether the status information is in a reference range (S620). Alternatively, the processor 120 may determine whether the status information is in the reference range (S620). The memory 140 may store the correlation between the status information and the biosignal, and the reference range may correspond to an abnormal range of the biosignal.

When it is determined that the status information is in the reference range (YES in S620), the controller 160 may activate the first sensor 111 to detect the biosignal (S630). Alternatively, the processor 120 may activate the first sensor 111 or the first sensor 111 may self-activate itself. The detected biosignal may be analyzed and provided to the user through the display module 130 or the like.

The correlation between a single biosignal and a single piece of status information has been described. However, the exemplary embodiment is not limited thereto. It is obvious that a correlation between a single biosignal and a plurality of pieces of status information may be calculated, and a correlation between a plurality of biosignals and a single piece of status information may be calculated. In addition, it is obvious that a part of a plurality of biosignal detection sensors may be adaptively selected and activated using the correlations.

Figure 7:
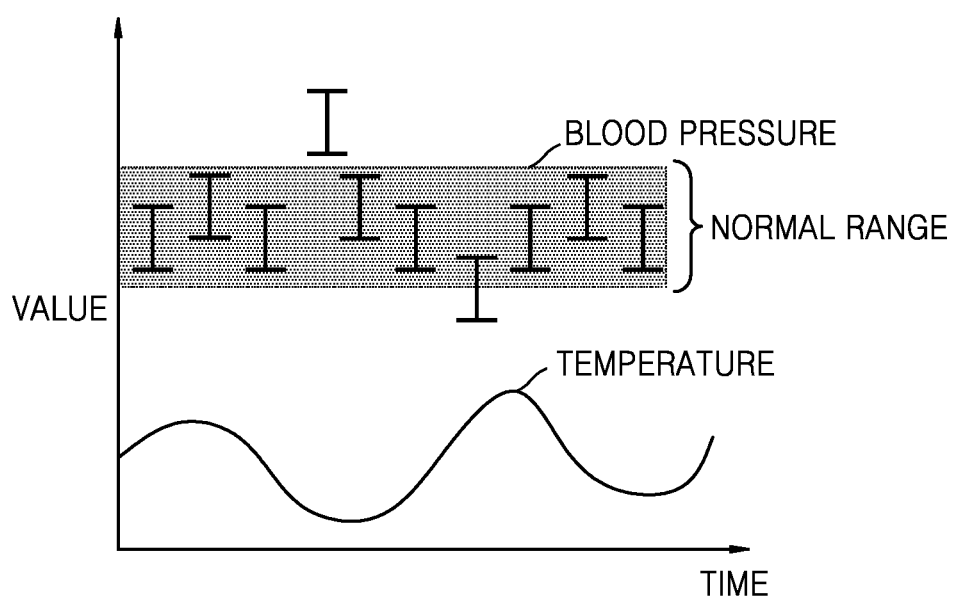
FIG. 7 is a graph of a correlation between status information and a biosignal, according to an exemplary embodiment.

FIG. 7 is a flowchart of a method of calculating a correlation between status information and a biosignal, according to an exemplary embodiment. As illustrated in FIG. 7, according to an exemplary embodiment, the biosignal processing apparatus may generate a blood pressure pattern related to a blood pressure as the biosignal, and a temperature pattern related to a temperature as the status information. The blood pressure pattern and the temperature pattern may be time-based functions. The biosignal processing apparatus may calculate a temperature value at the time when the blood pressure is out of a normal range. The biosignal processing apparatus may measure the blood pressure when the temperature at which the blood pressure is out of the normal range is detected.

As described above, according to the one or more of the above exemplary embodiment, referring to the correlation between the biosignal and the status information, the user may predict the biosignal from the status information. The biosignal may be selectively measured using the correlation between the biosignal and the status information.

In addition, other exemplary embodiments can also be implemented through computer readable code/instructions in/on a non-transitory medium, e.g., a computer readable medium, to control at least one processing element to implement any above described exemplary embodiment. The medium can correspond to any medium/media permitting the storage and/or transmission of the computer readable code.

The computer readable code can be recorded/transferred on a medium in a variety of ways, with examples of the medium including recording media, such as magnetic storage media (e.g., ROM, floppy disks, hard disks, etc.) and optical recording media (e.g., CD-ROMs, or DVDs), and transmission media such as Internet transmission media. Thus, the medium may be such a defined and measurable structure including or carrying a signal or information, such as a device carrying a bitstream according to one or more exemplary embodiments. The media may also be a distributed network, so that the computer readable code is stored/transferred and executed in a distributed fashion. Furthermore, the processing element could include a processor or a computer processor, and processing elements may be distributed and/or included in a single device.

It should be understood that the exemplary embodiments described therein should be considered in a descriptive sense only and not for purposes of limitation. Descriptions of features or aspects within each exemplary embodiment should typically be considered as available for other similar features or aspects in other exemplary embodiments.

While one or more exemplary embodiments have been described with reference to the figures, it will be understood by those of ordinary skill in the art that various changes in form and details may be made therein without departing from the spirit and scope as defined by the following claims.

What is claimed is:

1. A biosignal processing method by a biosignal processing apparatus, the method comprising:
   detecting a biosignal of a subject by the biosignal processing apparatus;
   determining, by the biosignal processing apparatus, at least one external environmental factor that influences a type of the detected biosignal, based on a lookup table storing a plurality of external factors in association with a plurality of types of biosignals;
   determining, by the biosignal processing apparatus, a degree of a correlation between the biosignal and a value of the determined at least one external environmental factor; and
   displaying the type of the detected biosignal, a value of the detected biosignal, the value of the determined at least one external environmental factor, and a percentage of the degree of the correlation on a same screen.

2. The biosignal processing method of claim 1, wherein the determining comprising determining the degree of the correlation in response to the at least one external environmental factor having a probability of influencing the type of the detected biosignal.

3. The biosignal processing method of claim 1, wherein the type of the detected biosignal is a blood pressure signal, and the determined at least one external environmental factor is a current temperature of an external environment, and
   wherein the displaying comprises displaying, on the same screen, the current temperature, the type indicating that the detected biosignal is the blood pressure signal, a value of the blood pressure signal, and the percentage of the degree of the correlation between the current temperature and the value of the blood pressure signal.

4. The biosignal processing method of claim 1, wherein the biosignal includes at least one of information about an amount of a material contained in the subject and information about a motion of the subject.

5. The biosignal processing method of claim 1, wherein the biosignal includes information about at least one of blood sugar, cholesterol, body fat, blood pressure, an electrocardiogram, ballistocardiography, photoplethysmography, and an electromyogram of the subject.

6. The biosignal processing method of claim 1, wherein the at least one external environmental factor includes at least one of a temperature of an external environment, a humidity of the external environment, and an atmospheric pressure of the external environment.

7. The biosignal processing method of claim 1, wherein the degree of the correlation represents a degree of a change in the biosignal according to a change in the value of the at least one external environmental factor.

8. The biosignal processing method of claim 1, wherein the degree of the correlation represents a range of the value of the at least one external environmental factor corresponding to a reference range of the biosignal.

9. The biosignal processing method of claim 1, wherein the determining comprises:
- generating a biosignal pattern based on the biosignal in time domain;
- generating an external environmental pattern based on the value of the at least one external environmental factor in the time domain; and
- determining the degree of the correlation between the biosignal pattern and the external environmental pattern.

10. The biosignal processing method of claim 9, further comprising correcting the biosignal pattern based on the external environmental pattern.

11. A biosignal processing apparatus comprising:
- a first sensor configured to detect a biosignal of a subject;
- a second sensor configured to determine at least one external environmental factor that influences a type of the detected biosignal based on a lookup table storing a plurality of external factors in association with a plurality of types of biosignals;
- a processor configured to determine a degree of a correlation between the biosignal and a value of the determined at least one external environmental factor; and
- a display configured to display the type of the detected biosignal, a value of the detected biosignal, the value of the determined at least one external environmental factor, and a percentage of the degree of the correlation on a same screen.

12. The biosignal processing apparatus of claim 11, wherein the processor is further configure to determine the degree of the correlation in response to the value of the at least one external environmental factor being determined as having a probability of influencing the biosignal.

13. The biosignal processing apparatus of claim 11, further comprising a controller configured to control the first sensor based on the value of the at least one external environmental factor and the degree of the correlation.

14. The biosignal processing apparatus of claim 13, wherein the controller is further configured to activate the first sensor to detect the biosignal in response to the value of the at least one external environmental factor being in a reference range.

15. The biosignal processing apparatus of claim 14, wherein the reference range corresponds to an abnormal range of the biosignal.

16. The biosignal processing apparatus of claim 11, wherein the type of the detected biosignal is a blood pressure signal, and the determined at least one external environmental factor is a current temperature of an external environment, and
- wherein the processor is further configured to control the display to display, on the same screen, the current temperature, the type indicating that the detected biosignal is the blood pressure signal, a value of the blood pressure signal, and the percentage of the degree of the correlation between the current temperature and the value of the blood pressure signal.

17. The biosignal processing apparatus of claim 11, wherein the biosignal includes at least one of information of an amount of a material contained in the subject and status information of an object contained in the subject.

18. The biosignal processing apparatus of claim 11, wherein the biosignal includes information about at least one of blood sugar, cholesterol, and body fat, blood pressure, an electrocardiogram, ballistocardiography, photoplethysmography, and an electromyogram of the subject.

* * * * *